United States Patent [19]

Bugaut et al.

[11] 4,420,637
[45] Dec. 13, 1983

[54] META-PHENYLENEDIAMINES

[75] Inventors: Andrée Bugaut, Boulogne; Jean-Jacques Vandenbossche, Aulnay-sous-Bois, both of France

[73] Assignee: L'Oreal, Paris, France

[21] Appl. No.: 53,813

[22] Filed: Jul. 2, 1979

[30] Foreign Application Priority Data

Jul. 12, 1978 [FR] France ................................ 78 20848

[51] Int. Cl.³ ...................... C07C 91/40; C07C 91/42
[52] U.S. Cl. ......................................... 564/443; 8/404; 8/406; 8/407; 8/409; 8/410; 8/412; 132/7
[58] Field of Search ...................... 260/573; 8/11, 404, 8/406, 407, 409, 410, 412; 564/443

[56] References Cited

U.S. PATENT DOCUMENTS

| | | | |
|---|---|---|---|
| 2,552,354 | 5/1951 | Glahn et al. ................... | 260/573 X |
| 3,970,423 | 7/1976 | Brody et al. .................... | 8/10.2 |
| 4,125,367 | 11/1978 | Bugaut et al. ................... | 8/11 |

FOREIGN PATENT DOCUMENTS

| | | | |
|---|---|---|---|
| 2458668 | 6/1975 | Fed. Rep. of Germany | 8/11 |
| 2507567 | 8/1975 | Fed. Rep. of Germany | 8/11 |
| 2507569 | 8/1975 | Fed. Rep. of Germany | 8/11 |
| 2628716 | 1/1977 | Fed. Rep. of Germany | 8/11 |

Primary Examiner—John Doll
Attorney, Agent, or Firm—Cushman, Darby & Cushman

[57] ABSTRACT

New-meta-phenylenediamines are described for use in dyeing keratin fibres, especially human hair. These have the general formula:

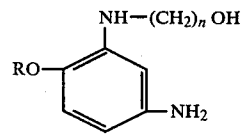

in which R represents an alkyl radical containing from 1 to 4 carbon atoms and n is an integer of from 1 to 3, or an acid salt thereof from 1 to 3 and include their acid salts.

34 Claims, No Drawings

META-PHENYLENEDIAMINES

This invention relates to novel meta-phenylenediamines useful as hair dyes.

In the field of dyeing keratin fibers, hair or fur, meta-phenylenediamines have long been known to play an important part; they form part of the class of compounds commonly referred to as "couplers". Couplers, in association with oxidative bases, such as para-phenylenediamines or para-aminophenols, give rise, in an oxidising alkaline medium, to coloured indamines, indoanilines or indophenols.

The association of meta-phenylenediamines with para-phenylenediamines, in an oxidising alkaline medium and, more particularly, in the presence of hydrogen peroxide, gives rise to indamines which are capable of imparting very strong blue colourations to keratin fibres. Meta-phenylenediamines, associated with para-aminophenols in an oxidising alkaline medium, given indolanilines which impart, to keratin fibres, red colourations which tend to purple shades. However, in practice, this category of couplers is restricted, in particular by virtue of the fact that it is only possible to use those few compounds which make it possible to obtain dyes which do not change with time under the action, in particular, of light or adverse weather conditions. Thus, 1-methyl-2-N-($\beta$-hydroxyethyl)-amino-4-aminobenzene provides light-unstable shades when it is associated with para-phenylenediamines and, in particular, with para-aminophenols.

The present invention provides a new class of meta-phenylenediamines which, with most para-phenylenediamines in an oxidising alkaline medium, impart light-resistant and weather-resistant blue colourations to the hair and which, moreover, give stable red colourations when they are associated with para-aminophenols.

The present invention provides a compound of the general formula

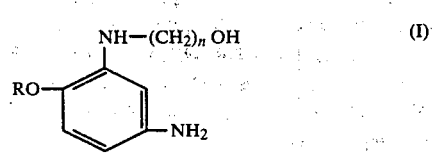

in which formula R represents a lower alkyl radical (i.e. containing from 1 to 4 carbon atoms) and n is an integer from 1 to 3 or an acid salt thereof, in particular a hydrochloride thereof.

The present invention also provides a dyeing composition for keratin fibres, and in particular for hair, the said composition containing, in a suitable carrier, at least one oxidative base and at least one compound of the formula (I) as coupler.

The meta-phenylenediamines according to this invention are advantageously used in dyeing compositions with the following oxidative bases:

A. the para-phenylenediamines of the general formula (II)

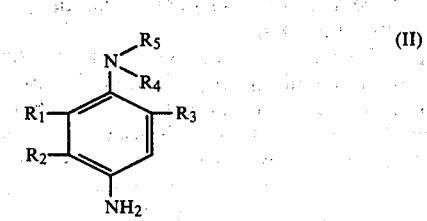

or the corresponding acid salts, in which formula $R_1$, $R_2$ and $R_3$ are identical or different and represent a hydrogen atom, an alkyl radical having from 1 to 4 carbon atoms or an alkoxy radical having from 1 or 2 carbon atoms, and $R_4$ and $R_5$ are identical or different and represent a hydrogen atom, an alkyl radical, a hydroxyalkyl radical, an alkoxyalkyl radical in which the alkoxy group contains from 1 to 2 carbon atoms, a carbamylalkyl radical, a mesylaminoalkyl radical, an acetylaminoalkyl radical, a ureidoalkyl radical or a carbethoxyaminoalkyl radical, the alkyl groups in $R_4$ and $R_5$ having from 1 to 4 carbon atoms, with the proviso that $R_1$ and $R_3$ represent hydrogen if $R_4$ and $R_5$ do not represent a hydrogen atom; or B. the para-aminophenols of the general formula (III)

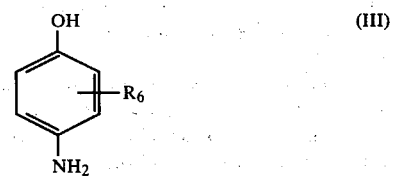

or the corresponding acid salts, in which formula $R_6$ represents a hydrogen atom, an alkyl radical containing from 1 to 4 carbon atoms, or a halogen atom such as chlorine or bromine.

It has been found that the use of the meta-phenylenediamines according to the invention with para-phenylenediamines and/or para-aminophenols makes it possible to obtain dyeing compositions which impart, to the hair, shades of good quality which do not change significantly in light, in adverse weather conditions or on washing.

Amongst the compounds of the formula (I) (and their acid salts), it has been found that particularly valuable results can be obtained with 2-N-($\beta$-hydroxyethyl)-amino-4-amino-1-methoxybenzene and 2-N-($\beta$-hydroxyethyl)-amino-4-amino-1-ethoxybenzene.

U.S. Pat. No. 2,083,308 describes meta-phenylenediamines which are similar to the compounds of the formula (I), but the primary amino group is acetylated. It has been found that these acetylated compounds can only be used in hair dyeing under very restricted conditions. In fact, 2-N-($\beta$-hydroxyethyl)-amino-4-acetylamino-1-methoxybenzene, in association with a para-phenylenediamine in an oxidising alkaline medium, does not dye the hair at a moderately alkaline pH of about 10, and it only imparts a weak green colouration to the hair at a weakly alkaline pH of about 8. On the other hand, we have been able to show that the non-acetylated compound, namely 2-N-($\beta$-hydroxyethyl)-amino-4-amino-1-methoxybenzene, in association with the same para-phenylenediamine and under identical operating conditions, imparts an intense blue colouration to the hair, regardless of whether the pH is 8 or 11.5 or within this range.

The dyeing compositions of this invention can also contain, in addition to the coupler (or couplers) of the formula (I) and the associated oxidative base (or bases), the following products, singly or in combination:

(1) other known couplers, for example resorcinol, meta-aminophenol, 2-methyl-5-aminophenol, 2-methyl-5-N-(β-hydroxyethyl)-aminophenol, 6-hydroxybenzomorpholine, 2,6-dimethyl-5-acetylaminophenol, 2-methyl-5-carbethoxyaminophenol, 2-methoxy-5-carbethoxyaminophenol and 2-methyl-5-ureidophenol;

(2) ortho-phenylenediamines and ortho-aminophenols optionally containing substituents on the nucleus or on the amine groups, or ortho-diphenol, it being possible for these products, by means of complex oxidation mechanisms, to lead to new coloured compounds, either by cyclisation with themselves or by reacting with the para-phenylenediamines;

(3) dyestuff precursors of the benzene series, containing, on the nucleus, at least three substituents which are hydroxyl, methoxy or amino groups, such as 2,6-diaminohydroquinone dihydrochloride, 2,6-diamino-4-N,N-(ethyl)-aminophenol trihydrochloride, 2,4-diaminophenol dihydrochloride, 1,2,4-trihydroxybenzene, 2,4,5-trihydroxytoluene or 4-methoxy-2-amino-N-(β-hydroxyethyl)-aniline;

(4) dyestuff precursors of the naphthalene series, such as 2-hydroxy-1,4-naphthoquinone and 5-hydroxy-1,4-naphthoquinone;

(5) leuco derivatives of indoanilines and of indophenols, such as 4,4'-dihydroxy-2-amino-5-methyldiphenylamine, 4,4'-dihydroxy-2-N-(β-hydroxyethyl)-amino-5-methyl-2'-chlorodiphenylamine, 2,4'-diamino-4-hydroxy-5-methyldiphenylamine, 2,4-dihydroxy-4'-N-(β-methoxyethyl)-aminodiphenylamine and 2,4-dihydroxy-5-methyl-4'-N-(β-methoxyethyl)-aminodiphenylamine;

(6) direct dyestuffs and, in particular, nitro benzene dyes, such as 1-N,N-(β-hydroxyethyl)-amino-3-nitro-4-N'-methylaminobenzene, 1-[N-methyl-N-(β-hydroxyethyl)]-amino-3-nitro-4-N'-(β-hydroxyethyl)-aminobenzene, 1-[N-methyl-N-(β-hydroxyethyl)]-amino-3-nitro-4-N'-methylaminobenzene, 3-nitro-4-N-(β-hydroxyethyl)-aminoanisole, 3-nitro-4-N-(β-hydroxyethyl)-aminophenol, 3-nitro-4-aminophenoxyethanol, 3-nitro-4-(N-methylamino)phenoxyethanol and 2-N-(β-hydroxyethyl)-amino-5-nitroanisole; and (7) various customary adjuvants such as penetrating agents, foaming agents, thickeners, antioxidants, alkalising or acidifying agents, perfumes, sequestering agents and film-forming products.

The pH of the dyeing compositions according to the invention is a basic pH generally 8 to 11.5 and preferably between 9 to 11.5. Amongst the alkalising agents which can be used, to provide such a pH there may be mentioned ammonia, alkylamines, such as ethylamine or triethylamine, alkanolamines, such as mono-, di- or tri-ethanolamine, alkylalkanolamines, such as methyldiethanolamine, sodium hydroxide or potassium hydroxide and sodium carbonate, potassium carbonate or ammonium carbonate. Amongst the acidifying agents which can be used, if necessary, there may be mentioned lactic acid, acetic acid, tartaric acid and phosphoric acid.

Anionic, cationic, non-ionic or amphoteric water-soluble surface-active agents can be incorporated in the composition according to the invention, and, in particular, alkylbenzenesulphonates, alkylnaphthalenesulphonates, sulphates, ether-sulphates and sulphonates of fatty alcohols, quaternary ammonium salts, such as trimethylcetylammonium bromide and cetylpyridinium bromide, diethanolamides of fatty acids, polyoxyethyleneated acids and alcohols and polyoxyethyleneated alkylphenols. The surface-active agents are preferably present in the composition according to the invention in an amount from 0.5 to 50% by weight and advantageously from 4 to 40% by weight.

Organic solvents can also be included in the composition according to the invention in order to solubilise compounds which would not otherwise be sufficiently water-soluble. Such solvents include ethanol, isopropanol, glycerol, glycols, such as ethylene glycol and propylene glycol, ethylene glycol monobutyl ether and diethylene glycol monoethyl ether and monomethyl ether. The solvents can advantageously be present in the composition in an amount from 1 to 40% by weight and preferably 5 to 30% by weight.

The thickening products which can be included in the composition according to the invention can be advantageously sodium alginate, gum arabic, cellulose derivatives, such as methylcellulose, hydroxyethylcellulose, hydroxypropylmethylcellulose and the sodium salt of carboxymethylcellulose, and acrylic acid polymers; inorganic thickeners, such as bentonite, can also be used. The thickeners are preferably present in an amount from 0.5 to 5% by weight, and advantageously from 0.5 to 3% by weight, relative to the total composition.

The antioxidants which can be incorporated in the composition include sodium sulphite, thioglycolic acid, sodium bisulphite, ascorbic acid and hydroquinone. These antioxidants are suitably present in the composition in an amount from 0.05 to 1.5% by weight, relative to the total weight of the composition.

The composition of the invention is generally mixed, at the time of use, with a sufficient amount of oxidising agent, in order to develop the colour on the keratin fibres. Suitable oxidising agents include hydrogen peroxide, per-salts, and urea peroxide.

In general, the compounds of the formula (I) are present in the dyeing composition in an amount from 0.005 to 2.5% by weight, relative to the total weight of the composition.

The dyeing composition according to the invention can be presented in the form of, for example, a liquid, a cream, a gel or an aerosol or in any other form which is suitable for dyeing keratin fibres.

The present invention also provides a process for dyeing keratin fibres, and in particular human hair, this process employing the dyeing composition defined above and being characterised in that the dyeing composition is applied to the keratin fibres at a temperature of from ambient temperature and about 37° C. and for, say, 5 to 45 minutes, and in that the keratin fibres are then rinsed and optionally shampooed, after which the said fibres are again rinsed.

The following Examples further illustrate the present invention.

EXAMPLE 1

Preparation of
2-N-(β-hydroxyethyl)-amino-4-amino-1-methoxybenzene dihydrochloride

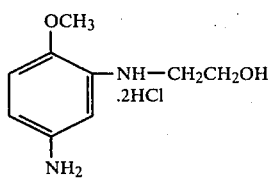

First step: Preparation of 2-N-(β-hydroxyethyl)-amino-4-nitro-1-methoxybenzene.

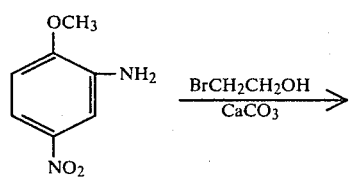

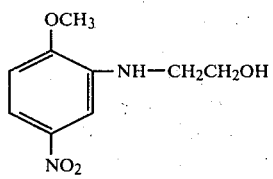

0.5 mol (84 g) of 2-amino-4-nitro-1-methoxybenzene is introduced into 252 cm³ of water. 0.5 mol (50 g) of calcium carbonate is added and the mixture is heated to 95° C. in a boiling water-bath. 1 mol (125 g) of glycol bromohydrin is then added, whilst stirring, and the temperature is then kept at 95° C. for three and a half hours, whilst stirring. 0.2 mol (25 g) of glycol bromohydrin and 0.1 (10 g) of calcium carbonate are then added and heating and stirring are then maintained for one and a half hours. A check is carried out to ensure that the reaction medium no longer contains any initial product detectable by chromatography. The reaction medium is filtered hot. 1,500 cm³ of ice-cooled water are added to the filtrate.

The expected product precipitates in the form of an oil which crystallises rapidly. Its melting point is equal to 67° C.

Elementary analysis of the product obtained gives the following results:

| Analysis | Calculated for C₉H₁₂N₂O₄ | Found |
|---|---|---|
| C % | 50.94 | 50.82 |
| H % | 5.70 | 5.98 |
| N % | 13.20 | 13.36 |

Second step: Preparation of 2-N-(β-hydroxyethyl)-amino-4-amino-1-methoxybenzene dihydrochloride 0.188 mol (39.8 g) of 2-N-(β-hydroxethyl)-amino-4-nitro-1-methoxybenzene, dissolved in 400 cm³ of ethanol, is hydrogenated under a pressure of 20 bars at a temperature of the order of 85° C., in the presence of 2 g of 10% strength palladium-on-charcoal. After one hour, the alcoholic solution is filtered in order to remove the catalyst. 70 cm³ of ethanol at −15° C., saturated with hydrogen chloride, are added to the filtrate, whilst stirring, the filtrate being cooled in a solid carbon dioxide bath.

The expected product precipitates in the form of the dihydrochloride.

The product is filtered off and dried in vacuo. It melts at 234° C. with decomposition.

Elementary analysis of the product obtained gives the following results:

| Analysis | Calculated for C₉H₁₆O₂N₂Cl₂ | Found |
|---|---|---|
| C % | 42.35 | 42.11 |
| H % | 6.27 | 6.23 |
| N % | 10.98 | 10.90 |
| Cl % | 27.84 | 27.67 |

EXAMPLE 2

Preparaton of
2-N-(β-hydroxyethyl)-amino-4-amino-1-ethoxybenzene dihydrochloride First step:

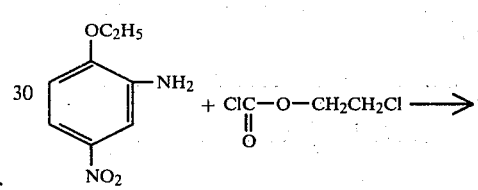

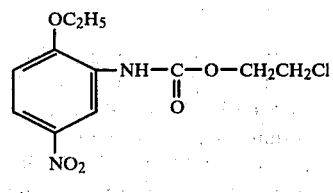

Second step:

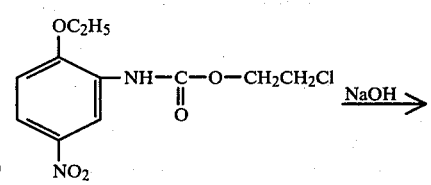

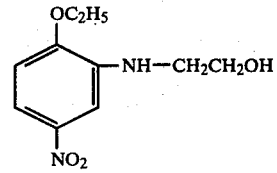

Third step:

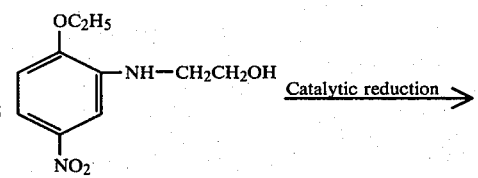

-continued

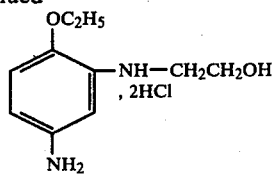

First step: Preparation of β-chloroethyl (2'-ethoxy-5'-nitrophenyl)-carbamate 0.1 mol (18.2 g) of 2-amino-4-nitro-1-ethoxybenzene is dissolved in 55 cm³ of dioxane. 0.055 mol (5.5 g) of calcium carbonate is added and the temperature is then raised to about 90° C. 0.11 mol (15.7 g) of β-chloroethyl chloroformate is then introduced, whilst stirring. When the addition is complete, stirring is maintained for half an hour at 90° C. After cooling, 200 cm³ of ice-cooled water are added to the reaction medium and the mixture is then acidified with hydrochloric acid until the pH is equal to 5.

The expected product precipitates. It is filtered off, washed with water and dried in vacuo. After recrystallisation from ethanol, its melting point is equal to 143° C.

Elementary analysis of the product obtained gives the following results:

| Analysis | Calculated for $C_{11}H_{13}N_2O_5Cl$ | Found |
|---|---|---|
| C % | 45.75 | 45.86 |
| H % | 4.51 | 4.73 |
| N % | 9.71 | 9.85 |

Second step: Preparation of 2-N-(β-hydroxyethyl)-amino-4-nitro-1-ethoxybenzene 0.075 mol (21.6 g) of the crude product obtained in accordance with the operation described in the first step is dissolved in 80 cm³ of ethanol under reflux. 27 cm³ of normal sodium carbonate solution are then added, whilst stirring. The reaction medium is kept under reflux for one hour, whilst stirring, and 100 cm³ of ice-cooled water are then added.

The expected product precipitates in the form of crystals. It is filtered off, washed with water and recrystallised from ethanol. After drying in vacuo, it melts at 107° C.

Elementary analysis of the product obtained gives the following results:

| Analysis | Calculated for $C_{10}H_{14}N_2O_4$ | Found |
|---|---|---|
| C % | 53.10 | 53.14 |
| H % | 6.19 | 6.22 |
| N % | 12.39 | 12.63 |

Third step: Preparation of 2-N-(β-hydroxethyl)-amino-4-amino-1-ethoxybenzene dihydrochloride The nitro derivative obtained in the preceding step is dissolved in ethanol (0.04 mol, that is to say 9.04 g, of nitro derivative in 36 cm³ of ethanol). 0.3 g of 10% strength palladium-on-charcoal is added as a catalyst. The nitro derivative is reduced by catalytic hydrogenation at 70° C. under a pressure of 75 bars for one hour. The mixture is filtered in order to remove the catalyst, and 15 cm³ of ethanol, saturated with hydrogen chloride, are then added to the filtrate.

After cooling to 0° C., the expected product, which has precipitated in the form of the dihydrochloride, is filtered off. The product is subsequently washed with alcohol and then with acetone and dried in vacuo. Its melting point is equal to 210° C.

Elementary analysis of the product obtained gives the following results:

| Analysis | Calculated for $C_{10}H_{18}N_2O_2Cl_2$ | Found |
|---|---|---|
| C % | 44.61 | 44.40 |
| H % | 6.69 | 6.75 |
| N % | 10.41 | 10.27 |

It should be noted that the process for the preparation of 2-N-(β-hydroxyethyl)-amino-4-amino-1-methoxybenzene dihydrochloride, described in Example 1, can also be applied to the preparation of 2-N-(β-hydroxyethyl)-amino-4-amino-1-ethoxybenzene dihydrochloride. However, the process described in Example 2 cannot be applied to the preparation of 2-N-(β-hydroxyethyl)-amino-4-amino-1-methoxybenzene dihydrochloride because a cyclisation takes place with the 2-N-(β-hydroxyethyl)-amino-4-nitro-1-methoxybenzene (obtained after the first preparation step in which glycol bromohydrin is reacted) in the presence of sodium hydroxide, and this leads to a morpholine ring-containing product and not to the expected one.

EXAMPLE 3

The following dyeing composition is prepared:

| | |
|---|---|
| 2-N—(β-Hydroxyethyl)-amino-4-amino-1-methoxybenzene dihydrochloride | 0.025 g |
| Para-phenylenediamine dihydrochloride | 0.018 g |
| Ethylene glycol monobutyl ether | 1.66 g |
| Lauryl alcohol containing 10.5 mols of ethylene oxide (per mol of alcohol) | 1.66 g |
| Product sold under the tradename "Carbopol 934" (an acrylic acid polymer having a molecular weight of 2 to 3 million, manufactured by the Société "Goodrich Chemical Co") | 0.66 g |
| Triethanolamine | 2.5 g |
| Mercaptosuccinic acid | 0.5 g |
| Water q.s.p. | 100 g |

The pH of this composition is equal to 9.9.

50 g of hydrogen peroxide of 20 volumes strength are added at the time of use.

When applied to bleached hair for 15 minutes at 25° C., this mixture imparts to the hair, after rinsing and shampooing, a wistaria colouration.

EXAMPLE 4

The following dyeing composition is prepared:

| | |
|---|---|
| 2-N—(β-Hydroxyethyl)-amino-4-amino-1-ethoxybenzene dihydrochloride | 0.538 g |
| Para-phenylenediamine dihydrochloride | 0.362 g |
| Carboxymethylcellulose | 2 g |
| Ammonium lauryl-sulphate | 5 g |
| Ammonium acetate | 1 g |
| Propylene glycol | 8 g |
| Aqueous solution of sodium bisulphite (39% strength) | 1 g |
| Ammonia solution (22° B strength) | 12 g |

The pH of this composition is equal to 10.1.

100 g of hydrogen peroxide of 20 volumes strength are added at the time of use.

When applied to 90% naturally white hair for 15 minutes at 27° C., this mixture imparts to the hair, after rinsing and shampooing, a purple colouration.

EXAMPLE 5

The following dyeing composition is prepared:

| | |
|---|---|
| 2-N—(β-Hydroxyethyl)-amino-4-amino-1-methoxybenzene dihydrochloride | 1.27 g |
| Para-phenylenediamine dihydrochloride | 1.27 g |
| Ethanolamides of copra fatty acids | 10 g |
| Aqueous solution of sodium bisulphite (39% strength) | 1 g |
| Ammonia solution (22° B strength) | 10 g |
| Water q.s.p. | 100 g | the pH of this composition is equal to 9.9.

When applied to bleached hair for 25 minutes at 25° C., this mixture imparts to the hair, after rinsing and shampooing, an extremely dark violet colouration.

EXAMPLE 6

The following dyeing composition is prepared:

| | |
|---|---|
| 2-N—(β-Hydroxyethyl)-amino-4-amino-1-ethoxybenzene dihydrochloride | 0.0135 g |
| Para-toluylenediamine dihydrochloride | 0.0196 g |
| Oxyethyleneated oleyl alcohol containing 2 mols of ethylene oxide | 5 g |
| Oxyethyleneated oleyl alcohol containing 4 mols of ethylene oxide | 10 g |
| Propylene glycol | 10 g |
| Triethanolamine | 1 g |
| Mercaptosuccinic acid | 0.05 g |
| Water q.s.p. | 100 g |

The pH of this composition is equal to 8.8.

50 g of hydrogen peroxide of 20 volumes strength are added at the time of use.

When applied to bleached hair for 20 minutes at ambient temperature, this mixture imparts to the hair, after rinsing and shampooing, a silvery light blue colouration.

EXAMPLE 7

The following dyeing composition is prepared:

| | |
|---|---|
| 2-N—(β-Hydroxyethyl)-amino-4-amino-1-methoxybenzene dihydrochloride | 1.275 g |
| Para-toluylenediamine dihydrochloride | 0.975 g |
| Nonylphenol containing 4 mols of ethylene oxide (a product sold under the tradename "Remcopal 334" by the Société "Gerland") | 20 g |
| Nonylphenol containing 9 mols of ethylene oxide (a product sold under the tradename "Remcopal 349" by the Société "Gerland") | 20 g |
| Thioglycolic acid | 0.8 g |
| Ammonia solution (22° B strength) | 10 g |
| Water q.s.p. | 100 g |

The pH of this composition is equal to 9.8.

100 g of hydrogen peroxide of 20 volumes strength are added at the time of use.

When applied to 90% naturally white hair for 25 minutes at ambient temperature, this mixture imparts to the hair, after rinsing and shampooing, a deep purplish-blue colouration.

EXAMPLE 8

The following dyeing composition is prepared:

| | |
|---|---|
| 2-N—(β-Hydroxyethyl)-amino-4-amino-1-methoxybenzene dihydrochloride | 1.53 g |
| 4-N,N—(β-Hydroxyethyl)-aminoaniline dihydrochloride | 1.62 g |
| Carboxymethylcellulose | 2 g |
| Ammonium lauryl-sulphate | 5 g |
| Ammonium acetate | 1 g |
| Propylene glycol | 8 g |
| Aqueous solution of sodium bisulphite (39% strength) | 1 g |
| Ammonia solution (22° B strength) | 12 g |
| Hydroquinone | 0.10 g |
| Water q.s.p. | 100 g |

The pH of this composition is equal to 9.8.

100 g of hydrogen peroxide of 20 volumes strength are added at the time of use.

When applied to bleached hair for 15 minutes at 25° C., this mixture imparts to the hair, after rinsing and shampooing, a very strong royal blue colouration.

EXAMPLE 9

The following dyeing composition is prepared:

| | |
|---|---|
| 2-N—(β-Hydroxyethyl)-amino-4-amino-1-ethoxybenzene dihydrochloride | 0.269 g |
| 2,6-Dimethyl-4-methoxy-para-phenylenediamine dihydrochloride | 0.239 g |
| Ammonium $C_{12}$-$C_{14}$—alkyl-sulphate (70% of $C_{12}$ and 30% of $C_{14}$) | 15 g |
| Lauryl alcohol containing 10.5 mols of ethylene oxide | 5 g |
| Ammonia solution (22° B strength) | 10 g |
| Aqueous solution of sodium bisulphite (39% strength) | 0.5 g |
| Water q.s.p. | 100 g |

The pH of this composition is equal to 10.

70 g of hydrogen peroxide of 20 volumes strength are added at the time of use.

When applied to 90% naturally white hair for 30 minutes at 30° C., this mixture imparts to the hair, after rinsing and shampooing, a silvery light blue-green grey colouration.

EXAMPLE 10

The following dyeing composition is prepared:

| | |
|---|---|
| 2-N—(β-Hydroxyethyl)-amino-4-amino-1-ethoxybenzene dihydrochloride | 1.076 g |
| 4-N—(β-Methoxyethyl)-aminoaniline dihydrochloride | 1.195 g |
| Nonylphenol containing 4 mols of ethylene oxide (sold under the tradename "Remcopal 334" by the Société "Gerland") | 18 g |
| Nonylphenol containing 9 mols of ethylene oxide (sold under the tradename "Remcopal 349" by the Société "Gerland") | 18 g |
| Thioglycolic acid | 0.8 g |
| Ammonia (22° B strength) | 4 g |
| Water q.s.p. | 100 g |

The pH of this composition is equal to 9.2.

100 g of hydrogen peroxide of 20 volumes strength are added at the time of use.

When applied to light chestnut hair for 30 minutes at ambient temperature, this mixture imparts to the hair, after rinsing and shampooing, a blue-black colouration.

EXAMPLE 11

The following dyeing composition is prepared:

| | |
|---|---|
| 2-N—(β-Hydroxyethyl)-amino-4-amino-1-methoxybenzene dihydrochloride | 1.53 g |
| 4-N—(β-Methoxyethyl)-aminoaniline dihydrochloride | 1.434 g |
| Diethanolamides of copra fatty acids | 10 g |
| Aqueous solution of sodium bisulphite (39% strength) | 0.8 g |
| Ammonia solution (22° B strength) | 10 g |
| Water q.s.p. | 100 g |

The pH of this composition is equal to 9.9.

100 g of hydrogen peroxide of 20 volumes strength are added at the time of use.

When applied to 90% naturally white hair for 20 minutes at 25° C., this mixture imparts to the hair, after rinsing and shampooing, a strong, rather dark, pure blue colouration.

EXAMPLE 12

The following dyeing composition is prepared:

| | |
|---|---|
| 2-N—(β-Hydroxyethyl)-amino-4-amino-1-methoxybenzene dihydrochloride | 2.55 g |
| 2,6-Dimethyl-5-methoxy-para-phenylenediamine dihydrochloride | 2.39 g |
| Nonylphenol containing 4 mols of ethylene oxide (sold under the tradename "Remcopal 334" by the Société "Gerland") | 20 g |
| Nonylphenol containing 9 mols of ethylene oxide (sold under the tradename "Remcopal 349" by the Société "Gerland") | 20 g |
| Thioglycolic acid | 0.8 g |
| Ammonia solution (22° B strength) | 10 g |
| Water q.s.p. | 100 g |

The pH of this composition is equal to 9.9.

100 g of hydrogen peroxide of 20 volumes strength are added at the time of use.

When applied to bleached hair for 20 minutes at 25° C., this mixture imparts to the hair, after rinsing and shampooing, a midnight blue colouration.

EXAMPLE 13

The following dyeing composition is prepared:

| | |
|---|---|
| 2-N—(β-Hydroxyethyl)-amino-4-amino-1-methoxybenzene dihydrochloride | 1.275 g |
| Para-aminophenol | 0.545 g |
| Carboxymethylcellulose | 2 g |
| Ammonium lauryl-sulphate | 5 g |
| Ammonium acetate | 1 g |
| Propylene glycol | 8 g |
| Aqueous solution of sodium bisulphite (39% strength) | 1.2 g |
| Ammonia solution (22° B strength) | 12 g |
| Water q.s.p. | 100 g |

The pH of this composition is equal to 9.9.

100 g of hydrogen peroxide of 20 volumes strength are added at the time of use.

When applied to bleached hair for 20 minutes at 25° C., this mixture imparts to the hair, after rinsing and shampooing, an extremely luminous, slightly purple, red colouration.

EXAMPLE 14

The following dyeing composition is prepared:

| | |
|---|---|
| 2-N—(β-Hydroxyethyl)-amino-4-amino-1-ethoxybenzene dihydrochloride | 1.34 g |
| Para-aminophenol | 0.545 g |
| Nonylphenol containing 4 mols of ethylene oxide (sold under the tradename "Remcopal 334" by the Société "Gerland") | 12 g |
| Nonylphenol containing 9 mols of ethylene oxide (sold under the tradename "Remcopal 349" by the Societe "Gerland") | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| Propylene glycol | 6 g |
| Aqueous solution of sodium bisulphite (39% strength) | 1 g |
| Ammonia solution (22° B strength) | 10 g |
| Ethylenediaminetetraacetic acid | 0.12 g |
| Water q.s.p. | 100 g |

The pH of this composition is equal to 10.2.

100 g of hydrogen peroxide of 20 volumes strength are added at the time of use.

When applied to 90% naturally white hair for 15 minutes at 27° C., this mixture imparts to the hair, after rinsing and shampooing, a very red copper colouration.

EXAMPLE 15

The following dyeing composition is prepared:

| | |
|---|---|
| 2-N—(β-Hydroxyethyl)-amino-4-amino-1-methoxybenzene dihydrochloride | 1.785 g |
| 4-[N—ethyl-N—(β-mesylaminoethyl)]-aminoaniline dihydrochloride | 2.31 g |
| 1-Phenyl-3-methylpyrazol-5-one | 0.15 g |
| Aqueous solution of sodium bisulphite (39% strength) | 1 g |
| Nonylphenol containing 4 mols of ethylene oxide (sold under the tradename "Remcopal 334" by the Société "Gerland") | 20 g |
| Nonylphenol containing 9 mols of ethylene oxide (sold under the tradename "Remcopal 349" by the Société "Gerland") | 20 g |
| Ammonia solution (22° B strength) | 10 g |
| Water q.s.p. | 100 g |

The pH of this composition is equal to 9.9.

100 g of hydrogen peroxide of 20 volumes strength are added at the time of use.

When applied to bleached hair for 20 minutes at 25° C., this mixture imparts to the hair, after rinsing and shampooing, an intense pure blue colouration.

EXAMPLE 16

The following dyeing composition is prepared:

| | |
|---|---|
| 2-N—(β-Hydroxyethyl)-amino-4-amino-1-methoxybenzene dihydrochloride | 0.765 g |
| Para-phenylenediamine dihydrochloride | 0.905 g |
| Ortho-aminophenol | 0.218 g |
| Diethanolamides of copra fatty acids | 10 g |
| Aqueous solution of sodium bisulphite (39% strength) | 0.8 g |
| Ammonia solution (22° B strength) | 10 g |
| Water q.s.p. | 100 g |

The pH of this composition is equal to 9.9.

When applied to 95% naturally white hair for 20 minutes at 25° C., this mixture imparts to the hair, after rinsing and shampooing, a dark violet colouration.

EXAMPLE 17

The following dyeing composition is prepared:

| | |
|---|---|
| 2-N—(β-Hydroxyethyl)-amino-4-amino-1-methoxybenzene dihydrochloride | 1.27 g |
| Para-phenylenediamine dihydrochloride | 1.27 g |
| Para-aminophenol | 0.4 g |
| Diethanolamides of copra fatty acids | 10 g |
| Ammonia solution (22° B strength) | 12 g |
| Sodium bisulphite solution (39% strength) | 1 g |
| Hydroquinone | 0.20 g |
| Water q.s.p. | 100 g |

The pH of this composition is equal to 9.8.

When applied to bleached hair for 25 minutes at 27° C., this mixture imparts to the hair, after rinsing and shampooing, a purplish-blue black colouration.

EXAMPLE 18

The following dyeing composition is prepared:

| | |
|---|---|
| 2-N—(β-Hydroxyethyl)-amino-4-amino-1-methoxybenzene dihydrochloride | 0.61 g |
| Resorcinol | 0.5 g |
| Meta-aminophenol | 1 g |
| Para-phenylenediamine dihydrochloride | 4.6 g |
| Para-aminophenol | 0.1 g |
| Ortho-aminophenol | 1.1 g |
| Carboxymethylcellulose | 2 g |
| Ammonium lauryl-sulphate | 5 g |
| Ammonium acetate | 1 g |
| Propylene glycol | 8 g |
| Aqueous solution of sodium bisulphite (39% strength) | 1 g |
| Ammonia solution (22° B strength) | 12 g |
| Water q.s.p. | 100 g |

The pH of this composition is equal to 9.7.

100 g of hydrogen peroxide of 20 volumes strength are added at the time of use.

When applied to 90% naturally white hair for 20 minutes at 25° C., this mixture imparts to the hair, after rinsing and shampooing, a black colouration with a violet sheen.

EXAMPLE 19

The following dyeing composition is prepared:

| | |
|---|---|
| 2-N—(β-Hydroxyethyl)-amino-4-amino-1-methoxybenzene dihydrochloride | 0.2 g |
| Meta-aminophenol | 0.2 g |
| 2-Methyl-5-N—(β-hydroxyethyl)-aminophenol | 0.16 g |
| 3-N,N—(β-hydroxyethyl)-aminoaniline dihydrochloride | 0.1 g |
| 2-N—(β-Hydroxyethyl)-amino-4-nitrophenol | 0.15 g |
| Para-aminophenol | 0.5 g |
| Para-phenylenediamine dihydrochloride | 0.1 g |
| Carboxymethylcellulose | 2 g |
| Ammonium lauryl-sulphate | 5 g |
| Ammonium acetate | 1 g |
| Propylene glycol | 8 g |
| Aqueous solution of sodium bisulphite (39% strength) | 1 g |
| Ammonia solution (22° B strength) | 12 g |
| Water q.s.p. | 100 g |

The pH of this composition is equal to 10.2.

80 g of hydrogen peroxide of 20 volumes strength are added at the time of use.

When applied to 90% naturally white hair for 30 minutes at 27° C., this mixture imparts to the hair, after rinsing and shampooing, a mahogany colouration.

EXAMPLE 20

The following dyeing composition is prepared:

| | |
|---|---|
| 2-N—(β-Hydroxyethyl)-amino-4-amino-1-methoxybenzene dihydrochloride | 0.05 g |
| Resorcinol | 0.12 g |
| Meta-aminophenol | 0.12 g |
| Para-aminophenol | 0.25 g |
| 4-N,N—(β-Hydroxyethyl)-aminoaniline dihydrochloride | 0.10 g |
| 3-Nitro-4-N—(β-hydroxyethyl)-aminophenol | 0.04 g |
| Nonylphenol containing 4 mols of ethylene oxide (sold under the tradename "Remcopal 334" by the Société "Gerland") | 12 g |
| Nonylphenol containing 9 mols of ethylene oxide (sold under the tradename "Remcopal 349" by the Société "Gerland") | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| Ethylenediaminetetraacetic acid | 0.12 g |
| Aqueous solution of sodium bisulphite (39% strength) | 1.2 g |
| Ammonia solution (22° B strength) | 10 g |
| Water q.s.p. | 100 g |

The pH of this composition is equal to 10.3.

80 g of hydrogen peroxide of 20 volumes strength are added at the time of use.

When applied to 90% naturally white hair for 25 minutes at 27° C., this mixture imparts to the hair, after rinsing and shampooing, a very luminous golden beige colouration.

EXAMPLE 21

The following dyeing composition is prepared:

| | |
|---|---|
| 2-N—(β-Hydroxyethyl)-amino-4-amino-1-methoxybenzene dihydrochloride | 0.30 g |
| Resorcinol | 0.20 g |
| 2,6-Dimethyl-3-acetylaminophenol | 0.10 g |
| Para-aminophenol | 0.20 g |
| 2,6-Dimethyl-3-methoxy-para-phenylenediamine dihydrochloride | 0.50 g |
| 2-N—(β-Hydroxyethyl)-amino-5-nitroanisole | 0.06 g |
| Oxyethyleneated oleyl alcohol containing 2 mols of ethylene oxide | 4.5 g |
| Oxyethyleneated oleyl alcohol containing 4 mols of ethylene oxide | 4.5 g |
| Diethanolamides of copra fatty acids | 9 g |
| Oxyethyleneated oleylamine containing 12 mols of ethylene oxide (sold under the tradename "Ethomeen O12" by the Société "Armour Hess" Chemical Ltd") | 4.5 g |
| Propylene glycol | 3.6 g |
| Butylglycol | 8 g |
| Ethanol | 5.4 g |
| Aqueous solution of sodium bisulphite (39% strength) | 0.9 g |
| Ammonia solution (22° B strength) | 10 g |
| Water q.s.p. | 100 g |

The pH of this composition is equal to 9.7.

60 g of hydrogen peroxide of 20 volumes strength are added at the time of use.

When applied to 90% naturally white hair for 20 minutes at 27° C., this mixture imparts to the hair, after rinsing and shampooing, a pearlescent pinkish beige colouration.

EXAMPLE 22

The following dyeing composition is prepared:

| | |
|---|---|
| 2-N—(β-Hydroxyethyl)-amino-4-amino-1-methoxybenzene dihydrochloride | 0.3 g |
| Resorcinol | 0.2 g |
| Meta-aminophenol | 0.22 g |
| 6-Hydroxybenzomorpholine | 0.3 g |
| Para-aminophenol | 0.5 g |
| 4-(N—Ethyl-N—mesylaminoethyl)-aminoaniline dihydrochloride | 0.3 g |
| Mercaptosuccinic acid | 1.5 g |
| Oxyethyleneated oleyl alcohol containing 2 mols of ethylene oxide | 4.25 g |
| Oxyethyleneated oleyl alcohol containing 4 mols of ethylene oxide | 8.50 g |
| Propylene glycol | 8.50 g |
| Ammonia solution (22° B strength) | 15 g |
| Water q.s.p. | 100 g |

The pH of this composition is equal to 10.2.

90 g of hydrogen peroxide of 20 volumes strength are added at the time of use.

When applied to 90% naturally white hair for 25 minutes at 27° C., this mixture imparts to the hair, after rinsing and shampooing, a deep chestnut colouration.

EXAMPLE 23

The following dyeing composition is prepared:

| | |
|---|---|
| 2-N—(β-Hydroxyethyl)-amino-4-amino-1-ethoxybenzene dihydrochloride | 0.315 g |
| Meta-aminophenol | 0.5 g |
| 2-Methyl-5-aminophenol | 0.225 g |
| 2-Methyl-5-N—(β-hydroxyethyl)-aminophenol | 0.2 g |
| Para-aminophenol | 0.5 g |
| Para-toluylenediamine dihydrochloride | 0.8 g |
| 4-(N—Ethyl-N—mesylaminoethyl)-aminoaniline dihydrochloride | 1.2 g |
| 2-N—(β-Hydroxyethyl)-amino-5-nitroanisole | 0.345 g |
| Nonylphenol containing 4 mols of ethylene oxide (sold under the tradename "Remcopal 334" by the Société "Gerland") | 12 g |
| Nonylphenol containing 9 mols of ethylene oxide (sold under the tradename "Remcopal 349" by the Société "Gerland") | 15 g |
| Oxyethyleneated oleyl alcohol containing 2 mols of ethylene oxide | 1.5 g |
| Oxyethyleneated oleyl alcohol containing 4 mols of ethylene oxide | 1.5 g |
| Propylene glycol | 6 g |
| Ethylenediaminetetraacetic acid | 0.12 g |
| Aqueous solution of sodium bisulphite (39% strength) | 1.2 g |
| Ammonia solution (22° B strength) | 10 g |
| Water q.s.p. | 100 g |

The pH of this composition is equal to 9.6.

100 g of hydrogen peroxide of 20 volumes strength are added at the time of use.

When applied to naturally golden sand-coloured hair for 15 minutes at 28° C., this mixture imparts to the hair, after rinsing and shampooing, a chestnut colouration.

EXAMPLE 24

The following dyeing composition is prepared:

| | |
|---|---|
| 2-N—(βHydroxyethyl)-amino-4-amino-1-ethoxybenzene dihydrochloride | 0.16 g |
| 2-N—(β-Hydroxyethyl)-amino-4-amino-1-methoxybenzene dihydrochloride | 0.051 g |
| 6-Hydroxybenzomorpholine | 0.21 g |
| Resorcinol | 0.4 g |
| Para-phenylenediamine dihydrochloride | 1.5 g |
| 4-N—(β-Methoxyethyl)-aminoaniline dihydrochloride | 1 g |
| Para-aminophenol | 0.6 g |
| Nonylphenol containing 4 mols of ethylene oxide (sold under the tradename "Remcopal 334" by the Société "Gerland") | 16 g |
| Nonylphenol containing 9 mols of ethylene oxide (sold under the tradename "Remcopal 349" by the Société "Gerland") | 16 g |
| Mercaptosuccinic acid | 1 g |
| Ammonia solution (22° B strength) | 10 g |
| Water q.s.p. | 100 g |

The pH of this composition is equal to 9.5.

90 g of hydrogen peroxide of 20 volumes strength are added at the time of use.

When applied to 90% naturally white hair for 25 minutes at 28° C., this mixture imparts to the hair, after rinsing and shampooing, a medium chestnut colouration with a golden sheen.

EXAMPLE 25

The following dyeing composition is prepared:

| | |
|---|---|
| 2-N—(β-Hydroxyethyl)-amino-4-amino-1-methoxybenzene dihydrochloride | 0.5 g |
| 2-Methyl-5-aminophenol | 0.35 g |
| Resorcinol | 0.25 g |
| Para-aminophenol | 0.6 g |
| 4-N—(β-Methoxyethyl)-aminoaniline dihydrochloride | 0.8 g |
| N—Methyl-para-aminophenol sulphate | 0.45 g |
| 2-N—(β-Hydroxyethyl)-amino-5-nitrophenol | 0.25 g |
| 1-N,N—(β-Hydroxyethyl)-amino-3-nitro-4-N'-methylaminobenzene | 1 g |
| Ammonium $C_{12}$—$C_{14}$—alkyl-sulphate (70% of $C_{12}$ and 30% of $C_{14}$) | 15 g |
| Lauryl alcohol containing 10.5 mols of ethylene oxide | 5 g |
| Thioglycolic acid | 1 g |
| Ammonia solution (22° B strength) | 10 g |
| Water q.s.p. 100 g | |

The pH of this composition is equal to 9.6.

100 g of hydrogen peroxide of 20 volumes strength are added at the time of use.

When applied to 95% naturally white hair for 30 minutes at ambient temperature, this mixture imparts to the hair, after rinsing and shampooing, a golden chestnut colouration.

We claim:

1. A compound of the general formula

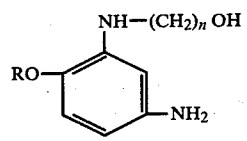 (I)

in which R represents an alkyl radical containing from 1 to 4 carbon atoms and n is an integer of from 1 to 3, or an acid salt thereof.

2. A compound according to claim 1 in which n is 2 and R is a methyl radical or a hydrochloride thereof.

3. A compound according to claim 1 in which n is 2 and R is an ethyl radical or a hydrochloride thereof.

4. A composition suitable for dyeing keratin fibres which comprises at least one oxidative base and at least one compound as defined in claim 1.

5. A composition according to claim 4, in which the compound of formula (I) is present in an amount from 0.005 to 2.5% by weight, relative to the total weight of the composition.

6. A composition according to claim 4, which has a pH from 8 to 11.5.

7. A composition according to claim 6 which has a pH from 9 to 11.5.

8. A composition according to claim 4 in which the oxidative base is a para-phenylenediamine or para-aminophenol.

9. A composition according to claim 8, in which the oxidative base is a para-phenylenediamine of the general formula:

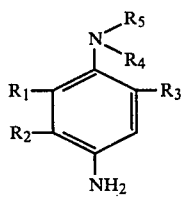

(II)

or an acid salt thereof, in which formula $R_1$, $R_2$ and $R_3$ are identical or different and represent a hydrogen atom, an alkyl radical having from 1 to 4 carbon atoms or an alkoxy radical having 1 or 2 carbon atoms, and $R_4$ and $R_5$ are identical or different and represent a hydrogen atom, an alkyl radical, a hydroxyalkyl radical, an alkoxyalkyl radical in which the alkoxy group contains 1 or 2 carbon atoms, a carbamylalkyl radical, a mesylaminoalkyl radical, an acetylaminoalkyl radical, a ureidoalkyl radical or a carbethoxyaminoalkyl radical, the alkyl groups in $R_4$ and $R_5$ having from 1 to 4 carbon atoms, with the proviso that $R_1$ and $R_3$ represent hydrogen if $R_4$ and $R_5$ do not represent a hydrogen atom.

10. A composition according to claim 8 in which the oxidative base is a para-aminophenol of the general formula

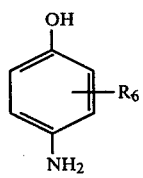

(III)

or an acid salt thereof, in which formula $R_6$ represents a hydrogen atom, an alkyl radical containing from 1 to 4 carbon atoms or a halogen atom.

11. A composition according to claim 4 which contains at least one ortho-phenylenediamine or ortho-aminophenol, which is unsubstituted or substituted on the nucleus or on the amino group, or ortho-diphenol.

12. A composition according to claim 4 which contain a leuco derivative of an indoaniline or indophenol.

13. A composition according to claim 12, in which the leuco derivative is 4,4'-dihydroxy-2-amino-5-methyldiphenylamine, 4,4'-dihydroxy-2-N-(β-hydroxyethyl)-amino-5-methyl-2'-chlorodiphenylamine, 2,4'-diamino-4-hydroxy-5-methyldiphenylamine, 2,4-dihydroxy-4'-N-(β-methoxyethyl)aminodiphenylamine or 2,4-dihydroxy-5-methyl-4'-N-(β-methoxyethyl)-aminodiphenylamine.

14. A composition according to claim 4 which contains at least one direct nitrobenzene dyestuff.

15. A composition according to claim 4 which contains at least one dyestuff precursor of the naphthalene series.

16. A composition according to claim 4 which contains at least one coupler other than a coupler of formula (I).

17. A composition according to claim 16 in which the other coupler is resorcinol, meta-aminophenol, 2-methyl-5-aminophenol, 2-methyl-5-N-(β-hydroxyethyl)-aminophenol, 6-hydroxybenzomorpholine, 2,6-dimethyl-5-acetylaminophenol, 2,6-dimethyl-5-carbethoxyaminophenol, 2-methoxy-5-carbethoxyaminophenol or 2-methyl-5-ureidophenol.

18. A composition according to claim 4 which at least one dyestuff precursor of the benzene series containing, on the nucleus, at least three substituents which are hydroxyl, methoxy or amino groups.

19. A composition according to claim 18, in which the dyestuff precursor is 2,6-diaminohydroquinone dihydrochloride, 2,6-diamino-4-N,N-ethylaminophenol trihydrochloride, 2,4-diaminophenol dihydrochloride, 1,2,4-trihydroxy benzene, 2,4,5-trihydroxytoluene or 4-methoxy-2-amino-N-(β-hydroxyethyl)-aniline.

20. A composition according to claim 4 which contains at least one penetrating agent, foaming agent, thickener, antioxidant, alkalising or acidifying agent, perfume, sequestering agent or film-forming product.

21. A composition according to claim 20 which contains ammonia, an alkylamine, an alkanolamine, an alkylalkanolamine, sodium or potassium hydroxide or sodium potassium or ammonium carbonate, or lactic, acetic, tartaric or phosphoric acid.

22. A composition according to claim 4 which contains at least one water-soluble surface-active agent which is an alkyl-benzenesulphonate, alkylnaphthalenesulphonate, sulphate, ether-sulphate or sulphonate of a fatty alcohol, a quaternary ammonium salt, a diethanolamide of a fatty acid, a polyoxyethyleneated acid or alcohol or a polyoxyethyleneated alkylphenol.

23. A composition according to claim 22 which contains from 0.5 to 50% by weight of surface-active agent, relative to the total weight of the composition.

24. A composition according to claim 4 which contains at least one organic solvent which is ethanol, isopropanol, glycerol, ethylene glycol, propylene glycol, ethylene glycol monobutyl ether, or diethylene glycol monoethyl ether or monomethyl ether.

25. A composition according to claim 24, which contains from 1 to 40% by weight of organic solvent, relative to the total weight of the composition.

26. A composition according to claim 4 which contains at least one thickener which is sodium alginate, gum arabic, methylcellulose, hydroxyethylcellulose, hydroxypropylmethyl cellulose, the sodium salt of carboxymethylcellulose, an acrylic acid polymer or bentonite.

27. A composition according to claim 26, which contains from 0.5 to 5% by weight of thickener, relative to the total weight of the composition.

28. A composition according to claim 4 which contains at least one antioxidant which is sodium sulphite, thioglycolic acid, sodium bisulphite, ascorbic acid or hydroquinone.

29. A composition according to claim 28, which contains from 0.05 to 1.5% by weight of anti-oxidant, relative to the total weight of the composition.

30. A composition according to claim 4 which is in the form of a liquid, a cream, a gel or an aerosol.

31. A composition according to claim 4 which is suitable for application to human hair.

32. Process for dyeing keratin fibres which comprises mixing, at the time of use, a composition as defined in claim 4 with at least one oxidising agent and applying the resulting mixture to the keratin fibres at a temperature from ambient temperature to about 30° C. and for about 5 to about 45 minutes, rinsing the keratin fibres and, optionally, shampooing and rinsing them.

33. Process according to claim 32 for dyeing human hair.

34. Process according to claim 32 in which the oxidising agent is hydrogen peroxide, urea peroxide or a persalt.

* * * * *